(12) United States Patent
Abt (10) Patent No.: US 10,682,202 B2
(45) Date of Patent: Jun. 16, 2020

(54) COMPOSITE ACTUATION HANDLES FOR A SURGICAL INSTRUMENT

(71) Applicant: Novartis AG, Basel (CH)

(72) Inventor: Niels Alexander Abt, Winterthur (CH)

(73) Assignee: Alcon Inc., Fribourg (CH)

( * ) Notice: Subject to any disclaimer, the term of this patent is extended or adjusted under 35 U.S.C. 154(b) by 0 days.

(21) Appl. No.: 15/470,122

(22) Filed: Mar. 27, 2017

(65) Prior Publication Data

US 2017/0281295 A1 Oct. 5, 2017

Related U.S. Application Data (60) Provisional application No. 62/315,278, filed on Mar. 30, 2016.

(51) Int. Cl.
*A61B 90/57* (2016.01)
*A61B 17/29* (2006.01)
(Continued)

(52) U.S. Cl.
CPC .............. *A61B 90/57* (2016.02); *A61B 17/08* (2013.01); *A61B 17/083* (2013.01); *A61B 17/1285* (2013.01); *A61B 17/2909* (2013.01); *A61B 17/30* (2013.01); *A61B 17/3217* (2013.01); *A61B 2017/0042* (2013.01); *A61B 2017/00367* (2013.01); *A61B 2017/00424* (2013.01); *A61B 2017/00964* (2013.01); *A61B 2017/292* (2013.01); *A61B 2017/2918* (2013.01);
(Continued)

(58) Field of Classification Search
CPC ...... A61B 2017/2918; A61B 2017/305; A61B 2017/00424; A61B 2017/0042; A61B 17/30; B25B 9/02; B25B 9/04; A45D 26/0066

USPC ........................................................ 294/99.2
See application file for complete search history.

(56) References Cited

U.S. PATENT DOCUMENTS 4,602,631 A * 7/1986 Funatsu ................. A61B 17/12
606/142
4,944,741 A 7/1990 Hasson
(Continued)

FOREIGN PATENT DOCUMENTS

DE 2428319 A1 1/1976
DE 29800876 U1 3/1998
(Continued)

OTHER PUBLICATIONS

Hyer, M.W. & Charette, R. F.: Innovative Design of Composite Structures: The Use of Curvilinear Fiber Format in Composite Structure Design); No. VPI-E-90-04, Mar. 1, 1990, pp. 1-17, XP055379597, Retrieved from the Internet: URL: https://ntrs.nasa.gov/archive/nasa/casi.ntrs.nasa.gov/1990010820.pdf (retrieved on Jun. 8, 2017; the whole document).

(Continued)

*Primary Examiner* — Diane D Yabut
*Assistant Examiner* — Majid Jamialahmadi (57) ABSTRACT

Systems and methods for forming a handle apparatus may include shaping a strip of composite material with a flexible central portion, two grips, and two end portions. The strip may be bent onto itself such that the end portions are fastened together by a fastening device. The handle apparatus may also include a hole disposed in the flexible central portion through which a tool actuator may be passed.

12 Claims, 7 Drawing Sheets

(51) Int. Cl.

| | | |
|---|---|---|
| *A61B 17/30* | (2006.01) | |
| *A61B 17/3217* | (2006.01) | |
| *A61B 17/128* | (2006.01) | |
| *A61B 17/08* | (2006.01) | |
| *A61B 17/00* | (2006.01) | |
| *A61B 17/3211* | (2006.01) | |

(52) U.S. Cl.
CPC .................. *A61B 2017/305* (2013.01); *A61B 2017/32113* (2013.01)

(56) References Cited

U.S. PATENT DOCUMENTS

| | | | |
|---|---|---|---|
| 5,192,106 A * | 3/1993 | Kaufman | B25B 9/02 294/16 |
| 5,242,746 A | 9/1993 | Bommier et al. | |
| 5,282,817 A * | 2/1994 | Hoogeboom | A61B 17/2909 606/167 |
| 5,376,407 A | 12/1994 | Feldman et al. | |
| 5,749,886 A * | 5/1998 | Abidin | A61B 17/3211 30/162 |
| 5,752,972 A | 5/1998 | Hoogeboom | |
| 5,795,524 A | 8/1998 | Basso, Jr. et al. | |
| 5,957,927 A * | 9/1999 | Magee | A61B 17/0218 606/104 |
| 2002/0077649 A1* | 6/2002 | Lasner | A61B 17/2841 606/174 |
| 2005/0192592 A1 | 9/2005 | Butler et al. | |
| 2009/0192359 A1* | 7/2009 | Hale | A61B 17/02 600/206 |
| 2014/0046345 A1* | 2/2014 | Armenteros | A61B 17/122 606/139 |

FOREIGN PATENT DOCUMENTS

| | | |
|---|---|---|
| WO | 2004093939 A2 | 11/2004 |
| WO | 2004093939 A3 | 2/2006 |
| WO | 2007149547 A2 | 12/2007 |

OTHER PUBLICATIONS

Wayback machine katalystsurgical pdf file; website snapshot dated Jan. 16, 2016; (accessed Aug. 27, 2018).

* cited by examiner

COMPOSITE ACTUATION HANDLES FOR A SURGICAL INSTRUMENT

TECHNICAL FIELD

The devices, systems, and methods disclosed herein relate generally to a composite handle that may be used with surgical instruments.

BACKGROUND

The introduction of modern technology in the medical field has led to great changes in the practice of medicine. Although medical equipment and machinery have evolved greatly due to gains in technology, many of the traditional implements used by medical professionals have remained nearly unchanged. For example, surgeons make wide use of traditional scalpels, scissors, forceps, and other hand-held devices. However, even these basic and traditional tools may be improved upon. For example, increasing demands on medical professionals has created the need for lighter and stronger tools. Composite materials have been applied to tool handles to address some of these needs. In particular, some tubular composite handles have been produced with holes disposed throughout to save weight. However, the use of composite materials in surgical tool handles has been limited to rigid, tubular handles which are generally used on tools, such as manipulators, without any moving parts. Furthermore, these tubular composite designs are often complex and difficult to manufacture. Accordingly, there is a need for lightweight, flexible handles that may be used with moving parts and are easily manufactured.

SUMMARY

The present disclosure relates generally to devices, systems, and methods relating to handles formed of composite materials.

In some implementations, a handle apparatus for a surgical instrument is provided. The handle apparatus may include a base component comprising a foldable strip of a first composite material that is bendable to form opposing sides of the handle apparatus. The base component may be sized and arranged to be grasped and squeezed by a hand during a surgical procedure. The base component may include a first grip having a proximal end and a distal end, a second grip having a proximal end and a distal end, and a flexible portion bendable to form an arcuate shape. The flexible portion may extend from the proximal end of the first grip to the proximal end of the second grip. The base component also may include a fastening mechanism connecting the distal end of the first grip to the distal end of the second grip.

In some implementations, the first grip and the second grip are formed from a second composite material that is different from the first composite material. The first grip and the second grip may be formed from the first composite material. In some implementations, the flexible portion has a first flexibility and the first and second grips have a second flexibility, wherein the first flexibility is greater than the second flexibility. A width of the first and second grips may be greater than a width of the flexible portion.

In some implementations, the fastening mechanism is one of a screw, bolt, brad, clip, rivet, or adhesive bond. The handle apparatus may further include a first hole disposed in a central portion of the flexible portion, and may include a tool adaptor which passes through the first hole. In some implementations, the first composite material comprises a plurality of fibers that may be bent around the first hole.

In some implementations, an actuation handle apparatus for a surgical instrument may include a handle and a tool adaptor. The handle may include a base component of a composite material. The base component may include a relatively more flexible region forming a flexible portion of the base component. The more flexible region may be bent in a U-shape and may have a first end and a second end. The base component may also include a relatively less flexible first grip extending from the first end of the more flexible region in a distal direction. The first grip may have a distal end portion. The base component may also include a relatively less flexible second grip extending from the second end of the more flexible region in a distal direction. The second grip may have a distal end portion. A fastening mechanism may connect the distal end portion of the first grip to the distal end portion of the second grip. The tool adaptor may be arranged to hold a working end of an actuatable surgical tool in a manner such that compression of the first and second grips axially displaces the tool adaptor.

In some implementations, the first grip and the second grip are formed from a different composite material than the more flexible region. A width of the first and second grips may be greater than a width of the more flexible region. In some aspects, a thickness of the first and second grips may be greater than a thickness of the more flexible region. In some implementations, the fastening mechanism is one of a screw, bolt, brad, clip, rivet, or adhesive bond. Depending on the implementation, the first and second grips may comprise one or more gripping features. For example, the first and second grips may have rounded outer edges. In some implementations, the actuation handle apparatus further comprises a first hole in the more flexible region, and the tool adaptor may extend from the fastening mechanism through the first hole.

In some implementations, a method of forming a handle is provided. The method may include forming a strip from a composite material having a first end section and a second end section, wherein the composite material comprises a plurality of fibers. The method also may include heating a section of the sheet; bending the sheet such that the first end section and the second end section are in physical contact; and securing the first end section to the second end section.

In some implementations, the method also may include securing the first end section to the second end section with one of a screw, bolt, brad, clip, or rivet. A first hole may be formed in the first end section and a second hole may be formed in the second end section. In some implementations, the method further may include passing a tool adaptor through a third hole and securing the tool adaptor to one or both of the first and second end sections.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the accompanying drawings and the following detailed description.

BRIEF DESCRIPTION OF THE DRAWINGS

The accompanying drawings illustrate implementations of the devices and methods disclosed herein and together with the description, serve to explain the principles of the present disclosure.

The accompanying drawings may be better understood by reference to the following detailed description.

DETAILED DESCRIPTION

For the purposes of promoting an understanding of the principles of the present disclosure, reference will now be made to the implementations illustrated in the drawings. Specific language will be used to describe the same. It will nevertheless be understood that no limitation of the scope of the disclosure is intended. Any alterations and further modifications to the described devices, systems, methods, and any further application of the principles of the present disclosure are fully contemplated as would normally occur to one skilled in the art to which the disclosure relates. In particular, it is fully contemplated that the features, components, and/or steps described with respect to one implementation may be combined with the features, components, and/or steps described with respect to other implementations of the present disclosure. For example, although explanatory references are made to "surgical tools," other applications are included within the scope of the present disclosure. For simplicity, in some instances the same reference numbers are used throughout the drawings to refer to the same or like parts.

The present disclosure relates generally to devices, systems, and methods relating to handles for hand-held tools. In particular, the present disclosure relates to surgical tool actuation handles. According to the implementations described herein, the handles may be formed from composite materials and may be configured for use with surgical tools. The handles described herein may offer benefits that cannot be obtained using conventional handles.

For example, the handles described herein may be operable for use with instruments having moving parts. In some implementations, the rigidity and flexibility of the handles described herein may be varied depending on the application of the handles. For example, the handles may be configured with a sufficient amount of rigidity to fully control the handles and attached devices as well as perform precise operations with the handles and attached devices. The handles described herein may also exhibit a range of flexibility, which may allow the handles to be used with tools requiring moving parts, for example, to actuate a forceps. Having some flexibility may also allow the handles to have a more ergonomic feel for a user. In some implementations, the rigidity and flexibility of the composite handles of the present disclosure may be variable. This variable flexibility may be accomplished through the use of different materials throughout the handles and in particular, through the use of composite materials. Furthermore, the use of composite materials may allow for tailored anisotropic behavior of the handles, allowing for a balance of rigidity and flexibility. The thickness and width of various components may also allow for variation of rigidity and flexibility in the handles of the present disclosure. The range of rigidity and flexibility may be helpful for using the handles with tools with non-moving parts, tools with moving parts, and/or tools requiring delicate care.

In addition, the handles of the present disclosure may be light due to the method by which they are formed as well as the composite materials used in their construction. This lightness may help to prevent user fatigue as well as improving manual precision as less motor units may be recruited to perform a task. Furthermore, the handles described in the present disclosure may include a limited number of constituent parts that are easily formed and assembled. Furthermore, the handles of the present disclosure may require a minimum number of machining steps in their production.

Furthermore, the present disclosure may provide techniques for manufacturing composite handles with holes while maintaining the integrity of composite materials, and in some cases, even strengthening the composite materials around the holes. As another advantage, the handles of the present disclosure may be inexpensive to produce and assemble, allowing them to be used once and discarded. This may protect medical professionals and patients while keeping costs low.

Figure 1:
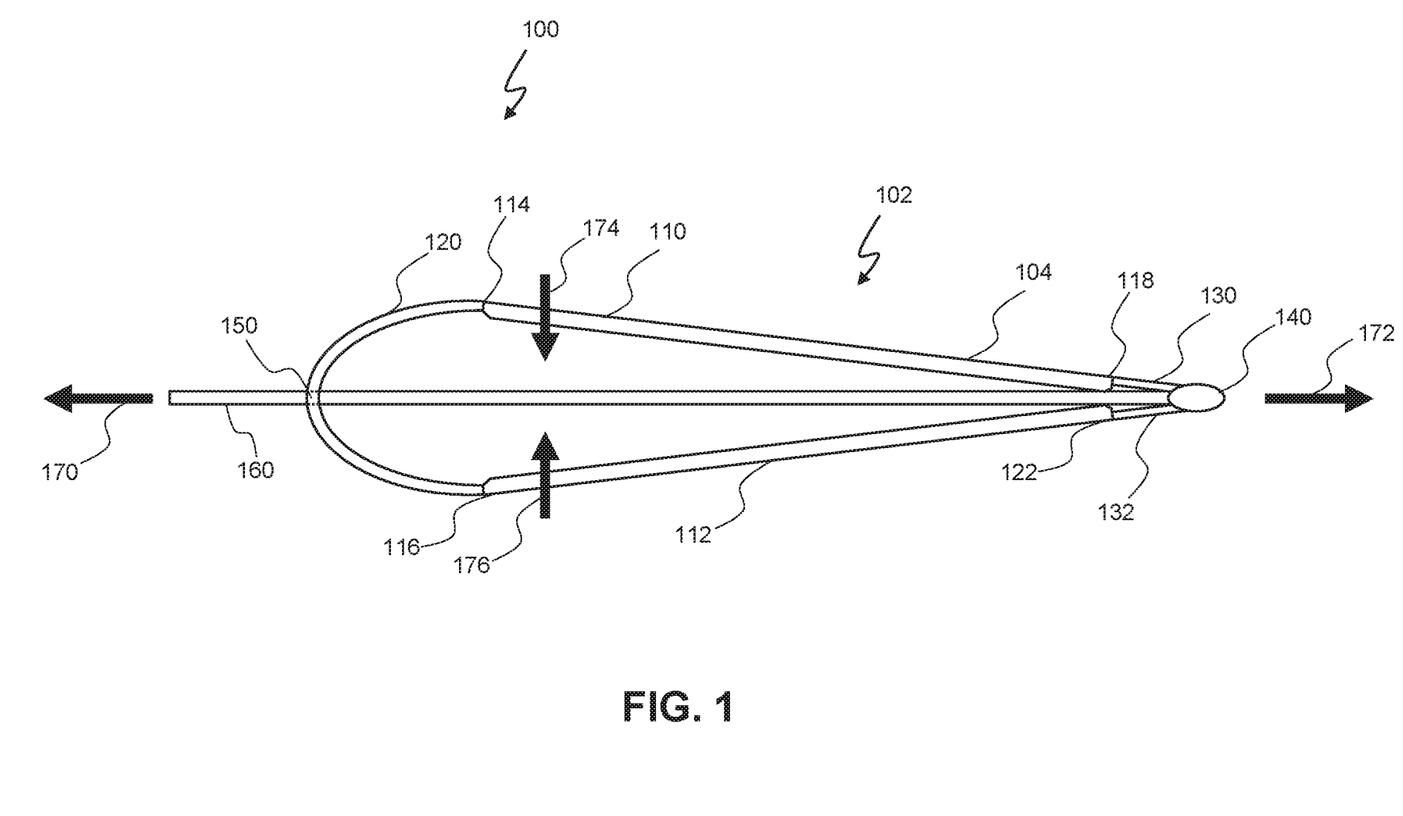
FIG. 1 illustrates a side view of an exemplary surgical tool actuation handle.

FIG. 1 illustrates a side view of an exemplary surgical tool actuation handle apparatus 100. The surgical tool actuation handle apparatus 100 may include a handle 102 and a tool adaptor 160. The handle 102 may include a base component 104 and a fastener 140. The base component 104 may include a flexible portion 120, a first grip 110, a second grip 112, a first end portion 130, a second end portion 132, and a hole 150. In some implementations, the surgical tool actuation handle apparatus 100 is produced by using a base component 104 in the shape of a foldable strip, bending the base component 104 onto itself, fastening the first and second end portions 130, 132 of the base component 104 with the fastener 140, and adding the tool adaptor 160. The base component will be described further herein.

The flexible portion 120 of the base component 104 may be configured to bend to allow the first and second end portions 130, 132 to be placed in physical contact. Accordingly, the flexible portion may bend, for example, within a range of 90 degrees to 270 degrees. In some implementations, the flexible portion may form an arcuate shape when bent. In some implementations, the flexible portion may bend more than 180 degrees to allow the end portions 130, 132 to come into contact with each other. In some implementations, the flexible portion 120 allows the first grip 110 and the second grip 112 to move closer together when pressure is applied to the surgical tool actuation handle apparatus 100. In some implementations, the flexible portion 120 comprises a composite material. In some implementations, the composite material is a pre-impregnated (prepreg) carbon or mixed fabric material. Additionally or alternatively, the composite material may include glass fibers, reinforced plastic, thermoplastics, epoxies, and other materials. The first and second grips 110, 112 may also be formed out of composite material. In some implementations, the first and second grips 110, 112 are less flexible than the flexible portion 120. In some implementations, this difference in flexibility is due to the thickness or width of the material of the constituent parts. For example, the thickness of the first and second grips 110, 112 may be greater than the thickness of the flexible portion 120. In another example, the thickness of the first and second grips 110, 112 and the flexible portion 120 is the same, but the first and second grips 110, 112 have a width that is less than the width of the flexible portion 120. In other implementations, the flexible portion 120 has a similar thickness and width as the first and second grips 110, 112, but the flexible portion 120 is more flexible than the first and second grips 110, 112 because it is formed from a more flexible material. Furthermore, by choosing the composite material mix, the bending stiffness of the flexible portion 120 and the grips 110, 112 may be tailored independently.

The curvature of various components of the surgical tool actuation handle apparatus 100 may affect its stiffness. For example, curving the first and second grips 110, 112 (e.g., by applying tension to the surgical tool actuation handle apparatus 100 during the joining of the first and second end portions 130, 132) may cause the stiffness of the first and second grips 110, 112 to be increased. This technique may allow for greater stiffness without adding weight by increasing the thickness of various components.

The first and second grips 110, 112 may include gripping features to aid a user in gripping the surgical tool actuation handle apparatus 100. For example, the first and second grips 110, 112 may include gripping features such as raised portions, ridges, pitted areas, holes formed therethrough, among other features. The gripping features may be formed during the shaping of the base component 104 of the composite handle. Additionally or alternatively, gripping features may be added after the first and second end portions 130, 132 are fastened together. In some implementations, the first and second grips 110, 112 and other portions of the handle are formed by cutting the composite materials, for example, by a water jet.

The first and second grips 110, 112 may be connected to the flexible portion 120 at their proximal ends 114, 116. Furthermore, the first grip 110 may be connected to the first end portion 130 at a distal end 118, and the second grip 112 may be connected to the second end portion 132 at a distal end 122. In some implementations, the first and second end portions 130, 132 may include fastening mechanisms such as holes, adhesive bonds, and welded joints. Other fastening mechanisms are also contemplated. In some implementations, fastening mechanisms of the first and second end portions 130, 132 may correspond, such as having matching holes. The fastener 140 may include any kind of fastening mechanism. Furthermore, the fastener 140 may include additional fastening mechanisms such as screws, bolts, clips, and/or adhesive bonds that may be added to the fastening mechanisms of the first and second end portions 130, 132. In the example of FIG. 1, the fastener 140 includes a bolt that passes through holes in the first and second end portions 130, 132. Other examples of fastening mechanisms are shown in FIG. 4.

Still referring to FIG. 1, the surgical tool actuation handle apparatus 100 may be actuated by pressing the first and second grips 110, 112 together in directions 174 and 176. This motion may decrease the radius of the flexible portion 120, which in turn may cause a longitudinal expansion of the surgical tool actuation handle apparatus 100 and associated axial motion in directions 170 and 172.

A tool adaptor 160 may be included in the surgical tool actuation handle apparatus 100. The tool adaptor 160 may be passed through the hole 150 in the flexible portion 120 and extend between the grips 110, 112 to the fastener 140. In some implementations, the tool adaptor 160 is affixed to the flexible portion 120 of the surgical tool actuation handle apparatus 100. In some implementations, the tool adaptor 160 may be a connector or shaft that connects to the body of a tool, such as a scalpel blade or a manipulator. In some implementations, the tool adaptor 160 may connect to a movable portion or the working end of a tool, such as the blades on scissors or the actuators on forceps. The tool adaptor 160 may be used with other articulable surgical tools. The tool adaptor 160 may be affixed to the first and second end portions 130, 132 and/or the fastener 140. The motion of the surgical tool actuation handle apparatus 100 in directions 170 and 172 as a result of squeezing or compressing the first and second grips 110, 112 in the lateral directions 174, 176 may be used to actuate tools with moving parts, such as scissors and forceps, for example. In some implementations, the tool adaptor 160 includes an inner shaft and an outer shaft, with the inner shaft extending through the hole 150 to the fastener 140. In FIG. 1, only the inner shaft is shown. The outer shaft may be fixed to the flexible portion 120 and may have a lumen in which the inner shaft may slide. Accordingly, when a user squeezes the actuation handle apparatus 100 in the lateral directions 174, 176, the outer shaft, connected to the flexible portion 120 moves in the axial direction 170 relative to the inner shaft which is connected to the fastener 140. In so doing, the outer shaft and the inner shaft axially displace relative to each other. This may actuate a tool, such as a forceps, for example.

FIGS. 2A-2D illustrate exemplary base components 104 that may be included in a surgical tool actuation handle apparatus 100. In some implementations, the base component 104 is a single strip comprising one or more composite materials that is shaped, bent, and fastened with a fastener 140 to form handle 102. The base component 104 shown in FIGS. 2A-2D may include a flexible portion 120, first and second grips 110, 112, and first and second end portions 130, 132, as shown in FIG. 1.

Figure 2A:
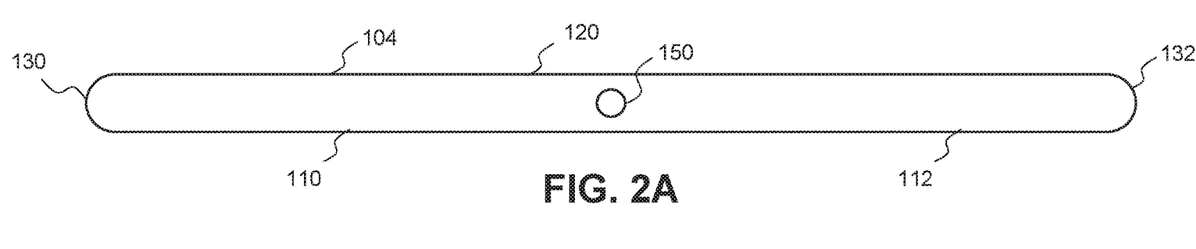
FIG. 2A is an illustration of an exemplary base component according to an implementation of the present disclosure.

In FIG. 2A, a base component 104 is depicted which may comprise prepreg carbon or mixed fabric composite material. In some implementations, the first and second end portions 130, 132 of the base component 104 are rounded. A hole 150 may be formed in the flexible portion 120 of the base component 104. This hole 150 may allow for greater flexibility of the flexible portion 120, as well as providing access for a tool adaptor 160 or other components.

Figure 2B:
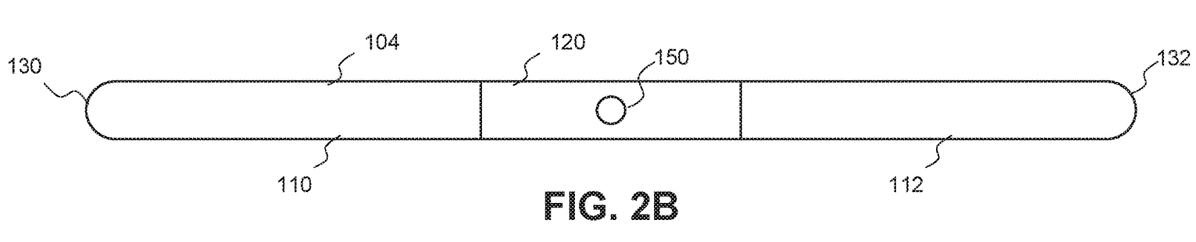
FIG. 2B is an illustration of an exemplary base component according to another implementation of the present disclosure.

FIG. 2B shows a base component 104 with a flexible portion 120 and a hole 150 formed in the center of the flexible portion 120. In some implementations, the flexible portion 120 may comprise a different material than the rest of the base component. For example, the flexible portion 120 may be formed with glass fibers, while the rest of the base component 104 comprises prepreg carbon composite material without glass fibers. The use of different materials for the flexible portion 120 may allow it to be more flexible and achieve greater curvature.

Figure 2C:
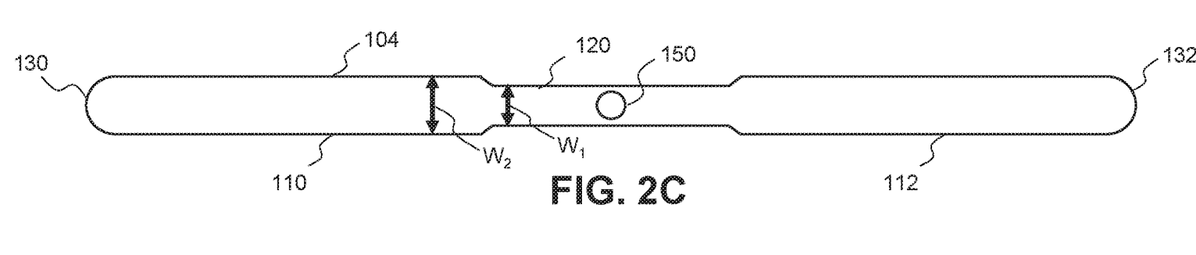
FIG. 2C is an illustration of an exemplary base component according to another implementation of the present disclosure.

FIG. 2C shows a base component 104 that includes a flexible portion 120 with a width $W_1$. In some implementations, width $W_1$ is smaller than a width $W_2$ of other portions of the base component 104 such as the grips 110, 112. In particular, the width $W_1$ of the flexible portion 120 may be narrowed by removing two trapezoid shaped portions of the base flexible portion 120. In other implementations, the width $W_1$ of the flexible portion 120 may be narrowed by removing portions of the flexible portion 120 with curved edges, elliptical shapes, rectangular shapes, or other shapes. The edges of the flexible portion 120 may be cut with a tool such as a water jet to decrease the width $W_1$ of the flexible portion 120. In some implementations, the width $W_1$ of the flexible portion 120 may be narrowed in such a way as to impart a desired amount of flexibility to the surgical tool actuation handle apparatus 100.

Figure 2D:
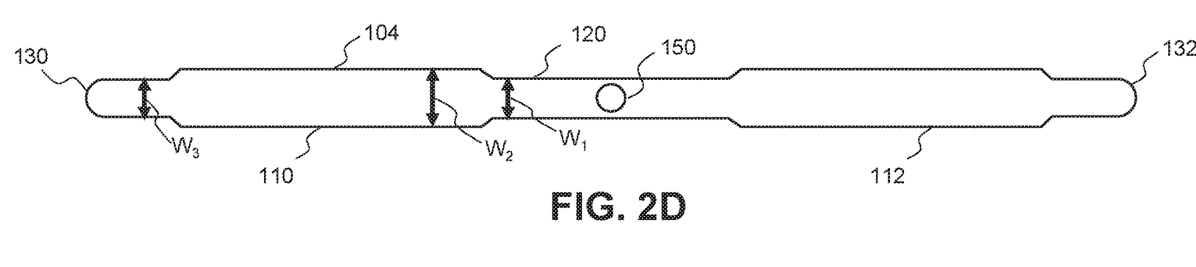
FIG. 2D is an illustration of an exemplary base component according to another implementation of the present disclosure.

FIG. 2D shows a base component 104 having a narrowed flexible portion 120 with width $W_1$ and narrowed first and second end portions 130, 132 with widths $W_3$. The narrowing of the flexible portion 120 and the first and second end portions 130, 132 may serve to define a first grip 110 and a second grip 112 therebetween, that have larger widths $W_2$. In some implementations, the first and second grips 110, 112 may allow a user to grasp and manipulate the surgical tool actuation handle apparatus 100. Furthermore, the larger width $W_2$ of the first and second grips 110, 112 in relation to other widths $W_1$, $W_3$ of the base component 104 may afford more rigidity to the first and second grips 110, 112. In some implementations, the greater flexibility of the flexible portion 120 and first and second end portions 130, 132 as compared to lesser flexibility of the first and second grips 110, 112 allows for greater precision in manipulating the surgical tool actuation handle apparatus 100.

Figure 3A:
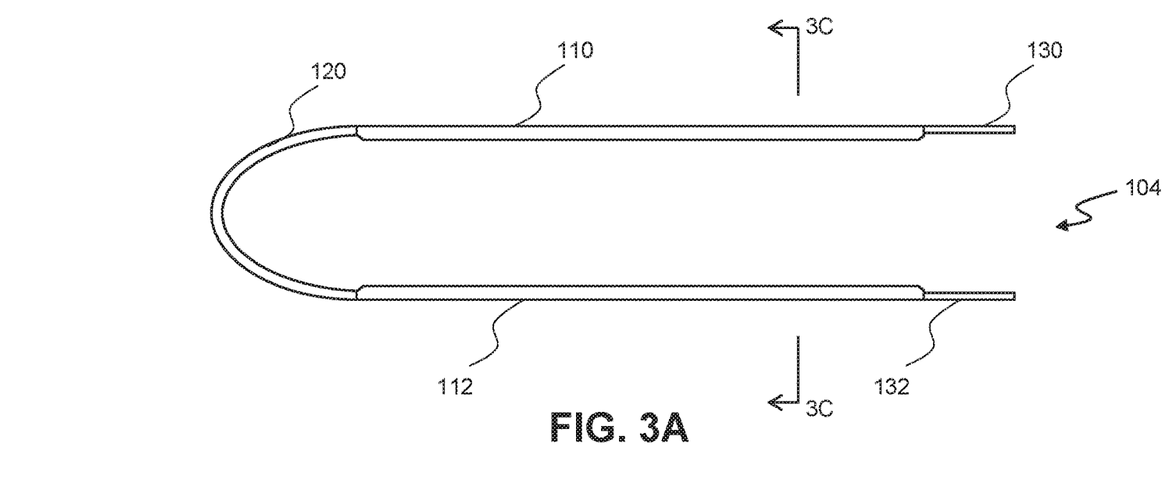
FIG. 3A is an illustration of a bent base component according to an implementation of the present disclosure.
Figure 3B:
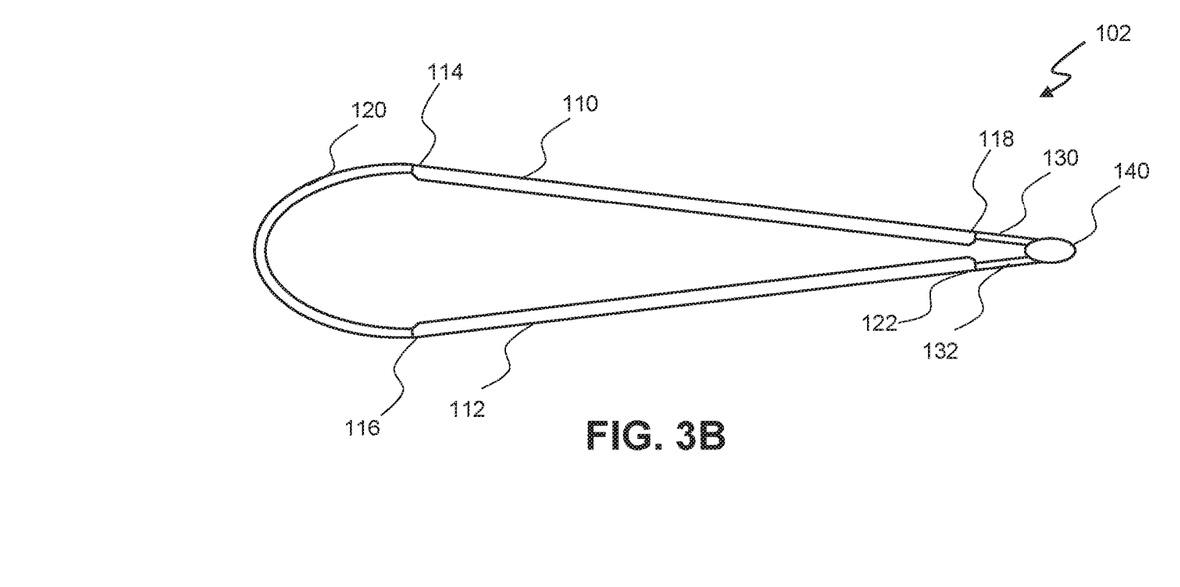
FIG. 3B is an illustration of a composite handle with fastened end portions according to an implementation of the present disclosure.

FIGS. 3A and 3B illustrate steps in the method of forming a handle 102 according to an implementation of the present disclosure. A bent base component 104 is shown in FIG. 3A that includes a flexible portion 120, first and second grips 110, 112, and first and second end portions 130, 132. In the example of FIG. 3A, the first and second grips 110, 112 are aligned to form a U-shape so that the flexible portion 120 has been bent. In some implementations, the handle 102 is not fully formed until the first and second end portions 130, 132 are fastened together with a fastener 140.

FIG. 3B shows a handle 102 with the base component 104 bent onto itself and first and second end portions 130, 132 joined together by a fastener 140. The flexible portion 120 may be bent with a greater curvature in FIG. 3B than in FIG. 3A. In some implementations, the first and second grips 110, 112 form a triangular shape that is wider at the proximal ends 114, 116 of the grips 110, 112 (e.g., where the grips 110, 112 connect to the flexible portion 120) than the distal ends 118, 122 of the first and second grips 110, 112. Although not shown, the handle 102 may be further modified. For example, the first and second grips 110, 112 may be further shaped or cut to a desired shape, such as having rounded edges. The grips 110, 112 may also be modified to include gripping features such as raised or lowered portions. Furthermore, a hole 150 may be drilled or cut into the flexible portion 120, and a tool adaptor 160 such as that depicted in FIG. 1 may be added to the handle 102.

Figure 3C:
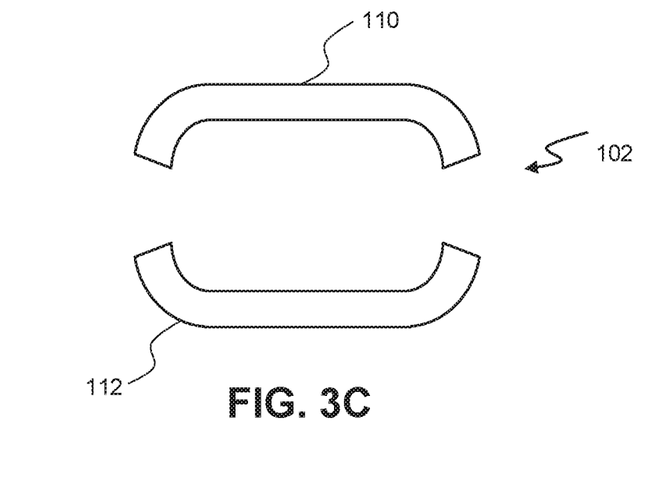
FIG. 3C is an illustration of a cross section of an exemplary composite handle according to an implementation of the present disclosure.
Figure 3D:
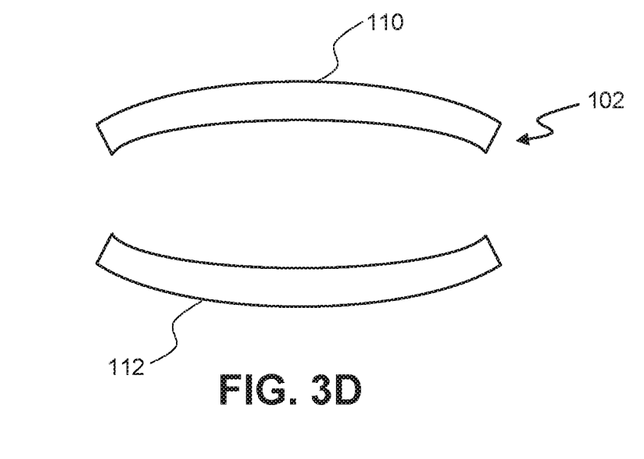
FIG. 3D is an illustration of a cross section of an exemplary composite handle according to another implementation of the present disclosure.
Figure 3E:
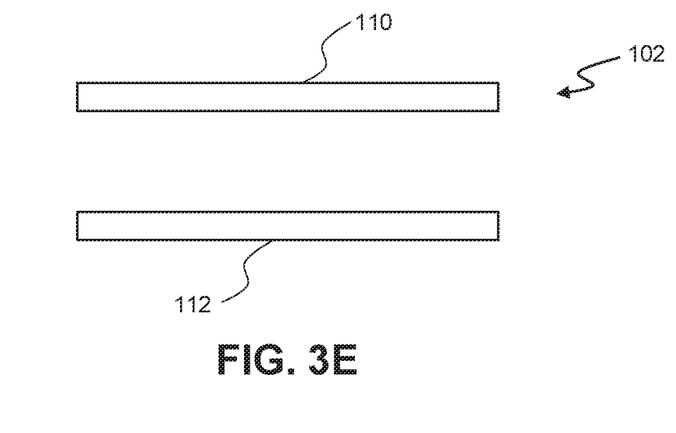
FIG. 3E is an illustration of a cross section of an exemplary composite handle according to another implementation of the present disclosure.

FIGS. 3C-3E show cross sectional views of the handle 102. FIG. 3C is a cross-section taken through the lines 3C-3C in FIG. 3A. In some implementations, one or more lateral edges of the handle 102, including the first and second grips 110, 112, are bent or curved laterally. This lateral curvature may help to add rigidity to various portions of the handle 102 without adding extra material and may help to minimize the overall weight of the handle 102. In other implementations, portions of the handle 102 may be formed from different materials or have different thicknesses. Variation in the curvature, thickness, and material of the handle 102 may help to fine tune the amount of rigidity and flexibility needed to perform different functions. Lateral curvature may be imparted to various portions of the handle 102 before or after the first and second end portions 130, 132 are joined together. Although FIGS. 3C-3D show lateral curvature in the first and second grips 110, 112, lateral curvature may also be imparted to other portions of the handle 102, including the flexible portion 120 and the first and second end portions 130, 132.

FIG. 3C shows a cross section of the handle 102 with the first and second grips 110, 112 having lateral curvature at the edges, but not the middle of the first and second grips 110, 112. The curvature of FIG. 3C may help to round the edges of the first and second grips 110, 112 to provide a comfortable grip for the user while increasing rigidity of the handle. FIG. 3D shows a cross section of the handle 102 with the first and second grips 110, 112 having lateral curvature across the width of the first and second grips 110, 112. FIG. 3E shows a cross section of the handle 102 with first and second grips 110, 112 that are not curved in a lateral direction.

FIG. 4 illustrates several examples of fastening mechanisms that may be used to form the fastener 140 of a composite handle, such as that depicted in FIGS. 1 and 3. In particular, one or more fastening mechanisms may be disposed around or between a first end portion 130 and a second end portion 132 of a base component 104. In the example of FIG. 4, various fastening mechanisms are shown in conjunction to the first end portion 130, although it will be understood that corresponding fastening mechanisms may be applied to a second end portion 132.

Figure 4A:
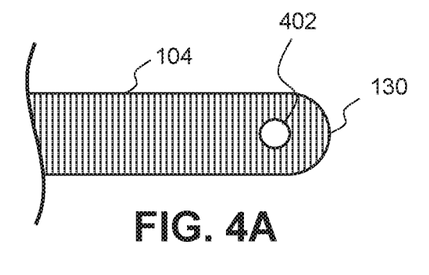
FIG. 4A is an illustration of an exemplary end fastening technique according to implementations of the present disclosure.

In one implementation shown in FIG. 4A, one or more holes 402 are disposed in the second end portion 130. The hole(s) 402 may be sized and arranged to receive a screw, bolt, brad, clip, rivet, or other fastening device to be passed therethrough to fasten the end portions 130, 132 together. Although shown as round or elliptical in the example of FIG. 4, the one or more holes 402 may be square, rectangular, hexagonal, or have other shapes to accommodate different types of fastening devices.

Figure 4B:
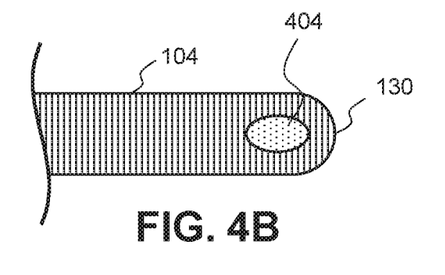
FIG. 4B is an illustration of another exemplary end fastening technique according to implementations of the present disclosure.

In another implementation shown in FIG. 4B, an adhesive bond 404 is disposed on a surface of the first end portion 130. This adhesive may be a composite adhesive, cement, or plastic. In some implementations, the adhesive bond is a composite bonding mechanism such as melting or fusing which may be used to fasten together the first and second end portions 130, 132.

Figure 4C:
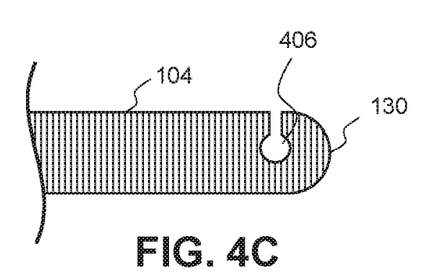
FIG. 4C is an illustration of another exemplary end fastening technique according to implementations of the present disclosure.

In another implementation shown in FIG. 4C, a side interface 406 is disposed in one or both of the first and second end portions 130, 132. This may allow a fastening device to be passed from the side to the middle of the first and second end portions 130, 132. The side interface 406 may allow for the quick installation or removal of a fastening device.

Figure 4D:
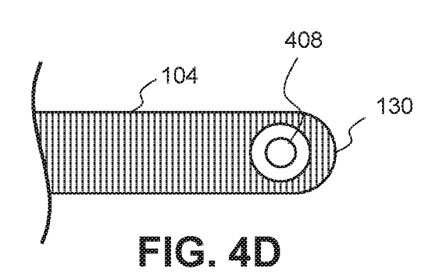
FIG. 4D is an illustration of another exemplary end fastening technique according to implementations of the present disclosure.

In another implementation shown in FIG. 4D, a hole reinforcement 408 is disposed on the first or second end portions 130, 132. In some implementations, the hole reinforcement 408 prevents a fastening mechanism from breaking through a portion of the first or second end portions 130, 132. The hole reinforcement 408 may be used in conjunction with another fastening device, such as a screw, bolt, clip, or rivet. The hole reinforcement 408 may allow for a more narrow first or second end portion 130, 132 than would be possible without reinforcement. The reinforcement of material around a hole is further discussed in reference to FIGS. 5A-5D.

Figure 4E:
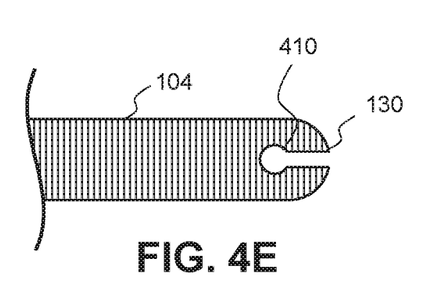
FIG. 4E is an illustration of another exemplary end fastening technique according to implementations of the present disclosure.

In another implementation shown in FIG. 4E, an end interface 410 is provided. Like the side interface 406, the end interface 410 may allow for a fastening device to be clipped into the first and/or second end portion 130, 132. Along with the side interface 406, the end interface 410 may allow for the use of removable fasteners on the surgical tool actuation handle apparatus 100.

Figure 4F:
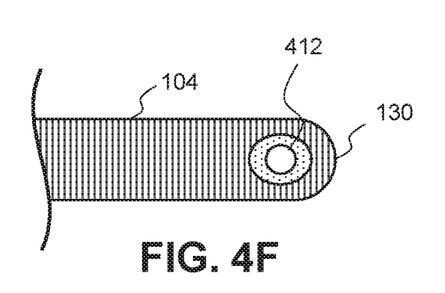
FIG. 4F is an illustration of another exemplary end fastening technique according to implementations of the present disclosure.

In another implementation shown in FIG. 4F, various combinations of fastening mechanisms are used. For example, a combination fastening device 412 may include an adhesive bond disposed around a hole. Such a combination may provide additional fastening strength. Other combinations are possible, including combining a side interface 406 and an end interface 410, reinforcing side interfaces 406 and end interfaces, 401, among others.

Figure 5A:
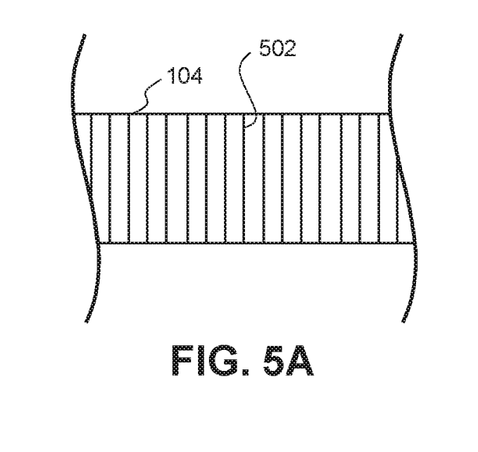
FIG. 5A is an illustration of a portion of a base component according to an implementation of the present disclosure.

FIGS. 5A-5D show exemplary techniques for forming a hole in a composite handle. FIG. 5A shows a portion of a base component 104 including a plurality of fibers 502. In some implementations, composite materials include fibers 502 that may be aligned in various directions throughout the material. In the example of 5A, the fibers 502 are aligned perpendicular to a longitudinal axis of the base component (i.e., in a vertical direction in FIG. 5A). The fibers 502 may include materials such as glass, carbon, metal, or other fibers. In some cases, the fibers 502 lend strength on the composite material. Forming holes in conventional composite devices may cause problems because fibers are generally cut when the holes are formed, weakening the composite material. This problem is addressed by the present disclosure by forming holes without cutting through fibers 502 or with minimal cutting or breaking of fibers.

Figure 5B:
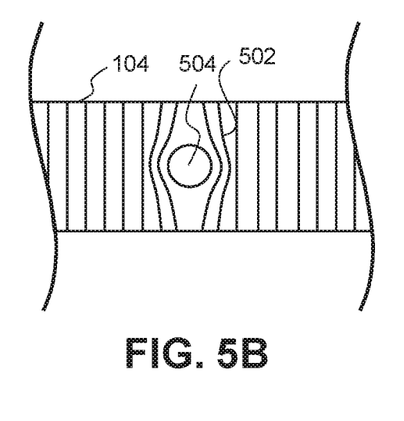
FIG. 5B is an illustration of a portion of a base component with a hole according to an implementation of the present disclosure.

FIG. 5B shows a hole 504 which has been formed in a portion of the base component 104. This hole may be the hole 150 of FIGS. 1 and 2, and/or the hole 402 of FIGS. 4A-4F. In some implementations, a prepreg carbon composite material is used in the base component 104 which may include aligned fibers 502. Like FIG. 5A, the fibers 502 are aligned vertically in FIG. 5B. The process of forming the hole 504 may include heating the composite material. A pointed device such a punch or die is used to form a hole 504 in the heated composite material. In some implementations, the formation of the hole bends the fibers 502 around the hole. The formation of the hole 504 during the curing process of the composite material may aid in bending the fibers 502 around the hole 504. In some implementations, the bent fibers 502 may lend additional strength to the hole 504 and act a self-reinforcement mechanism to protect the material around the hole 504 from damage due to movement of a fastener or other device extending through the hole 504.

Figure 5C:
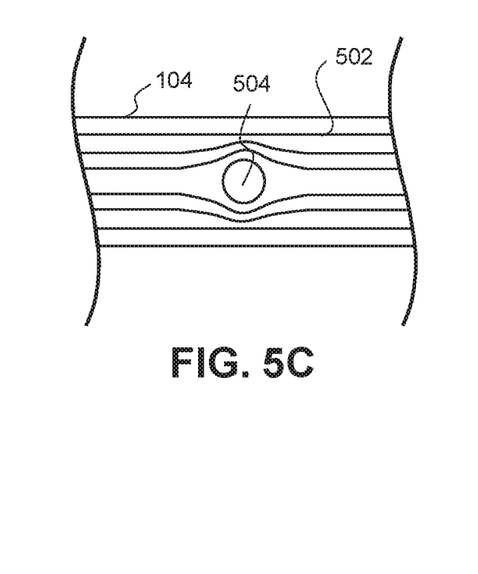
FIG. 5C is an illustration of a portion of a base component with a hole according to another implementation of the present disclosure.

FIG. 5C is an illustration of a portion of the base component 104 with a composite material that includes fibers 502 that are aligned parallel with a longitudinal axis of the base component 104 (i.e., in the horizontal direction). As in FIG. 5B, the formation of the hole 504 may allow for the bending of fibers 502 around a hole 504 without cutting them.

Figure 5D:
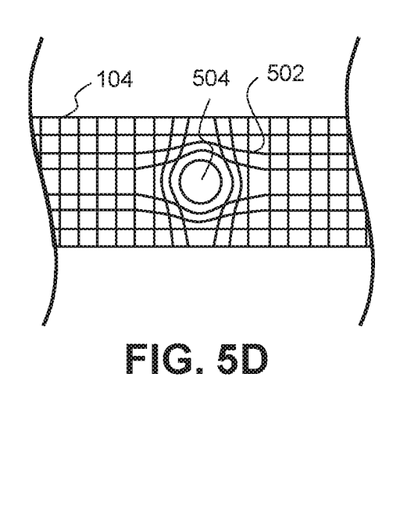
FIG. 5D is an illustration of a portion of a base component with a hole according to another implementation of the present disclosure.

FIG. 5D is an illustration of a portion of the base component 104 with a composite material that includes fibers 502 that are aligned both vertically and horizontally. The fibers 502 around the hole 504 may be bent or formed around the hole 504, lending additional strength to the base component 104.

Figure 6:
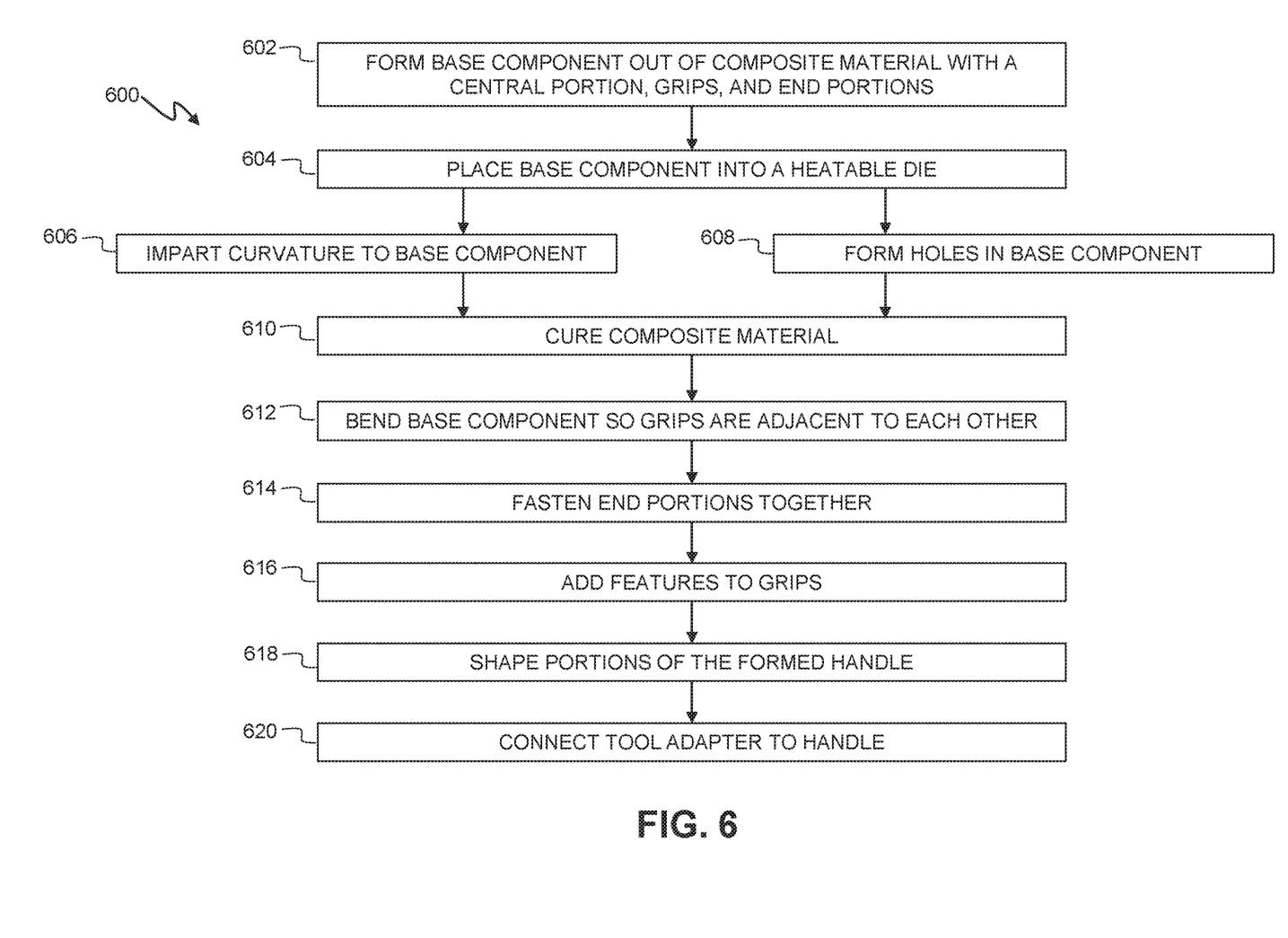
FIG. 6 is a flowchart of a method for forming a surgical tool actuation handle according to implementations of the present disclosure.

FIG. 6 is a flowchart of a method for forming a composite handle according to implementations of the present disclosure. The method is generally referred to by the reference number 600. It is understood that additional steps may be provided before, during, and after the steps of method 600, and that some of the steps described may be replaced or eliminated in other implementations of the method. In particular, 606, 608, 610, and 612 may be performed simultaneously or in various sequences as discussed below. In some embodiments, the steps may be performed in a different order than provided below.

At 602, the method 600 may include forming a base component out of composite material with a central portion, grips, and end portions. In some implementations, the base component is that depicted in FIGS. 2A-2D. The central portion, grips, and end portions may be the flexible portion 120, first and second grips 110, 112, and first and second end portions 130, 132, respectively, as depicted in FIGS. 1, 3A, and 3B. The base component may be formed from prepreg carbon composite material. All or a portion of the composite material may be uncured at 602. In some implementations, the base component may be formed from a strip of material comprising a single composite material with a uniform thickness throughout. Alternatively, the base component may include a second material for the grips and/or the central portion. This may allow the stiffness of various parts of the tool to be more precisely controlled. In particular, by choosing a mix of materials, the bending stiffness of the central portion and the rigidity of the grips may be tailored independently.

At 604, the method 600 may include placing the base component into a heatable die. In some implementations, the heatable die applies a desired form to the base component by applying heat and pressure to the base component. In some implementations, the heatable die is an autoclave or oven.

At 606, the method 600 may include imparting curvature to the base component. In some implementations, the central portion of the base component may be curved, as shown in FIG. 3A. Although not shown, the base component may also be curved in a direction perpendicular to its longitudinal axis and may appear curled or cupped along its length. The amount of curvature applied to the base component may be chosen to impart a specific amount of stiffness to the central portion and/or the grips.

At 608, the method 600 may include forming holes in the base component. These holes may be formed in the central portion, the end portions, or other locations therebetween. These holes may include hole 150 of FIGS. 1 and 2A-2D, the holes 402 of FIG. 4, and/or the hole 504 of FIGS. 5A-5D. In some implementations, composite fibers around the holes may be bent around the holes during their formation, such as shown in FIGS. 5A-5D. This may provide reinforcement to the area around the holes and afford the composite material greater strength than would be achieved by cutting through composite fibers while forming the holes.

At 610, the method 600 may include curing the composite material. In some implementations, the composite material is cured with heat from the heated die. In other implementations, the composite material is cured with ultraviolet light or chemical reactions that may or may not involve heat. The composite material may be cured after the composite material has been formed into a desired shape. Curing the composite material may include hardening epoxy within the composite material, fusing fibers together within the composite material, and/or adding a stiff coat to the exterior of the composite material.

At 612, the method 600 may include bending the base component so that the grips are adjacent to each other. In some implementations, pressure is applied with the heated die. In other implementations, the pressure is applied by devices after the base component has been removed from the die.

At 614, the method 600 may include fastening the end portions of the base component together. In some implementations, the end portions are modified before they are fastened together with features such as holes, adhesives, and reinforcements. These modifications may be made during any of 602, 608, and 610, for example. The end portions may be fastened together by any of the methods described in reference to FIG. 4, including fusing, melting, and the use of mechanical fasteners and adhesives. Other systems and techniques are also contemplated. At this point, the basic shape of the composite handle is formed.

At 616, the method 600 may include adding features to the grips. These features may include the gripping features as discussed previously. Additionally, one or more layers of a coating such as laminate may be applied to the grips. This may aid in gripping as well as modifying the flexibility of the handles. In some cases, adding features to the grips may increase the thickness of the grips as compared to the thicknesses of the central portion and the end portions. The difference in thicknesses may cause differences in flexibility, allowing for greater variation in flexibility across the base component.

At 618, the method 600 may optionally include shaping various portions of the formed composite handle. For example, the grips may be shaped by narrowing portions of the composite handle around the grips to create a more ergonomic shape. The grips may also be shaped with rounded edges. This shaping may be accomplished by a water jet or other cutting device. Furthermore, the central portion of the composite handle may be narrowed to increase the flexibility of the composite handle. Adaptions for tools such as holes and adhesive bonds may also be added to the composite handle.

At 620, the method 600 may include connecting a tool adaptor to the composite handle. In some implementations, the tool adaptor may be the tool adaptor 160 of FIG. 1. This tool adaptor may connect the composite handle to a tool face such as a manipulator, forceps, clamp, or scissors. In some implementations, the tool adaptor moves a portion of the tool when the handle is actuated by a user. In some cases, this actuation may be accomplished by pressing the grips of the composite handle together. This motion may close the blades on a pair of scissors or bring the ends of a pair of forceps together, for example.

The surgical tool actuation handle apparatus 100 as described herein offers advantages such as being lightweight, having variable flexibility, being suitable for use on surgical instruments with moving parts, being easily manufactured and assembled, and being suitable for disposable use.

Persons of ordinary skill in the art will appreciate that the implementations encompassed by the present disclosure are not limited to the particular exemplary implementations described above. In that regard, although illustrative implementations have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A handle apparatus for a surgical instrument comprising:
    a first grip having a proximal end and a distal end;
    a second grip having a proximal end and a distal end;
    a flexible, arcuate portion extending from the proximal end of the first grip to the proximal end of the second grip, the flexible, arcuate portion having a central portion and a first hole disposed in the central portion;
    a fastening mechanism connecting the distal end of the first grip to the distal end of the second grip via first and second end portions connected to the respective distal ends of the first and second grips; and
    a tool adapter extending through the first hole of the central portion of the flexible, arcuate portion;
    wherein the flexible, arcuate portion comprises a first composite material;
    wherein the first and second grips are sized and arranged to be grasped and squeezed toward a longitudinal axis of the handle apparatus by a hand during a surgical procedure; and
    wherein squeezing the first and second grips toward the longitudinal axis of the handle apparatus translates the central portion of the flexible, arcuate portion away from the distal ends of the first and second grips.

2. The handle apparatus of claim 1, wherein the first grip and the second grip are formed from a second composite material that is different from the first composite material.

3. The handle apparatus of claim 1, wherein the first grip and the second grip are formed from the first composite material.

4. The handle apparatus of claim 1, wherein the flexible, arcuate portion has a first flexibility and the first and second grips have a second flexibility, wherein the first flexibility is greater than the second flexibility.

5. The handle apparatus of claim 1, wherein a width of the first and second grips is greater than a width of the flexible, arcuate portion.

6. The handle apparatus of claim 1, wherein the fastening mechanism is one of a screw, bolt, brad, clip, rivet, or adhesive bond.

7. The handle apparatus of claim 1, wherein the first composite material comprises a plurality of fibers, wherein the fibers are bent around the first hole.

8. The handle apparatus of claim 1, wherein the first composite material comprises pre-impregnated carbon.

9. The handle apparatus of claim 1, wherein the first composite material comprises a mixed fabric material.

10. The handle apparatus of claim 1, wherein the first composite material comprises glass fibers, reinforced plastic, thermoplastic, or epoxy.

11. The handle apparatus of claim 1, wherein a thickness of the first and second grips is greater than a thickness of the flexible, arcuate portion.

12. The handle apparatus of claim 1, wherein the tool adaptor extends from the fastening mechanism through the first hole.

\* \* \* \* \*